United States Patent
Floyd, III et al.

(10) Patent No.: US 10,307,719 B2
(45) Date of Patent: Jun. 4, 2019

(54) POLYMERIC INVERT EMULSIFIERS

(71) Applicant: Ethox Chemicals, LLC, Greenville, SC (US)

(72) Inventors: William C Floyd, III, Greenville, SC (US); Charles F Palmer, Jr., Greenville, SC (US)

(73) Assignee: Ethox Chemicals, LLC, Greenville, SC (US)

( * ) Notice: Subject to any disclaimer, the term of this patent is extended or adjusted under 35 U.S.C. 154(b) by 0 days.

(21) Appl. No.: 15/177,791

(22) Filed: Jun. 9, 2016

(65) Prior Publication Data

US 2016/0361699 A1     Dec. 15, 2016

Related U.S. Application Data

(60) Provisional application No. 62/174,689, filed on Jun. 12, 2015, provisional application No. 62/184,609, filed on Jun. 25, 2015.

(51) Int. Cl.
*A01N 25/04*   (2006.01)
*B01F 17/00*   (2006.01)
*C08G 65/22*   (2006.01)
*C09K 8/588*   (2006.01)
*C09K 8/36*   (2006.01)
*A01N 25/30*   (2006.01)

(52) U.S. Cl.
CPC .......... *B01F 17/0028* (2013.01); *A01N 25/30* (2013.01); *B01F 17/005* (2013.01); *C08G 65/22* (2013.01); *C09K 8/36* (2013.01)

(58) Field of Classification Search
CPC .... B01F 17/0028; B01F 17/005; A01N 25/30; C08G 65/22; C09K 8/36
See application file for complete search history.

(56) References Cited

U.S. PATENT DOCUMENTS

| | | |
|---|---|---|
| 4,203,877 A | 5/1980 | Baker |
| 6,399,254 B1 * | 6/2002 | Kono ................. C08G 65/2609 252/62.2 |

* cited by examiner

*Primary Examiner* — Alma Pipic
(74) *Attorney, Agent, or Firm* — Joseph T. Guy; Patent Filing Specialist, Inc.

(57) ABSTRACT

A polymeric invert emulsifier is provided which is particularly suitable for use in demanding environments.

30 Claims, No Drawings

POLYMERIC INVERT EMULSIFIERS

CROSS-REFERENCE TO RELATED APPLICATIONS

The present invention claims priority to U.S. Provisional Patent Application Nos. 62/174,689 filed Jun. 12, 2015; 62/181,809 filed Jun. 19, 2015 and 62/184,609 filed Jun. 25, 2015 each of which is incorporated herein by reference.

FIELD OF THE INVENTION

The present invention is related to liquid nonionic invert emulsifiers comprising a plurality of substituted polyethers. More specifically the present invention is related to a branched polymeric liquid nonionic invert emulsifier having a preferably hydrophilic core and preferably hydrophobic pendant groups as a shell.

BACKGROUND

Polymeric emulsifiers suitable for use in forming water-in-oil emulsions, also known as invert or inverse emulsions, are highly valuable in many diverse fields. While multiple predominantly hydrophobic or low HLB surfactants are useful in forming these emulsions, polymeric compounds in particular have been found to be highly efficacious in this application. Among the commercially useful compounds are polyisobutylene succinimide (PIBSA) ethanolamides, as well as the branched and linear polyalkoxylene polyhydroxystearic acid copolymers described in U.S. Pat. No. 4,203,877. While these compounds form highly resilient inverse emulsions in a variety of applications ranging from cosmetics to explosives formulations, they are limited in some instances by their moderate structural integrity and labile chemical bonds. In particular, we have found that currently known inverse emulsifiers are degraded into non-useful components by the action of strong acids or bases. For example, we have found that emulsifiers essentially comprising polyethylene oxides copolymerized with polyhydroxystearic acid are incapable of forming stable invert emulsions in which the encapsulated phase is a hydrochloric acid solution, especially when exposed to elevated temperatures. Even though emulsions of this nature are currently of commercial interest in areas, such as oil recovery, there is no suitable material with a high degree of stability towards strongly alkaline or acidic environments. Specifically, we have produced emulsifiers comprised of ether linkages which withstand chemical assault under conditions in which ester and amide bonds are cleaved or degraded. We envision these emulsifiers as being particularly useful in harsh or demanding environments, such as under strongly acidic conditions at elevated temperatures such as those found in subterranean wells or within the machinery of industrial processes where these temperatures may be encountered. The surfactants described herein also benefit from additional favorable characteristics, such as ease and affordability of synthesis, an anticipated low toxicity, and a low pour point allowing room temperature processing. The present invention provides an invert emulsifier with improved functionality and decreased environmental impact.

SUMMARY

It is an object of the invention to provide an improved invert emulsifier.

A particular feature of the invention is the ability to provide an improved invert emulsifier which is chemically robust, cost effective and which demonstrates improved functionality as an emulsifier, especially in demanding environments.

These and other advantages, as will be realized, are provided in A polymeric invert emulsifier defined by Formula 1:

$$X[(CH_2CHR^1O)_n(CH_2CHR^2O)_mR^3]_o \qquad \text{Formula 1}$$

wherein X is a linking group derived from an organic compound containing at least two hydroxyl or amine groups capable of reacting with ethylene oxide;

each $R^1$ is independently —H or —$CH_3$;

each $R^2$ is independently —H, branched or linear aryl or alkyl moieties of 1-22 carbons which can be unsubstituted or substituted, and may also be —$CH_2OR^4$ groups such as those arising from the reaction of an alkyl or aryl glycidyl ether with the proviso that at least one $R^2$ is not hydrogen or methyl;

each $R^3$ is independently —H, unsubstituted or substituted aryl or alkyl hydrocarbon chains of 1-25 carbons which may be saturated or unsaturated or an ester group —C(=O)$R^5$;

$R^4$ is a branched or linear aryl or alkyl moiety of 1-22 carbons which can be substituted or unsubstituted;

$R^5$ is unsubstituted or substituted aryl or alkyl hydrocarbon chain of 1-25 carbons which may be saturated or unsaturated;

n is an integer of 3-300;

m is an integer of 2-300; and o is an integer of 2-12.

Yet another embodiment is provided in an emulsion comprising:

polymeric invert emulsifier defined by Formula 1:

$$X[(CH_2CHR^1O)_n(CH_2CHR^2O)_mR^3]_o \qquad \text{Formula 1}$$

wherein X is a linking group derived from an organic compound containing at least two hydroxyl or amine groups capable of reacting with ethylene oxide;

each $R^1$ is independently —H or —$CH_3$;

each $R^2$ is independently —H, branched or linear aryl or alkyl moieties of 1-22 carbons which can be unsubstituted or substituted, and may also be —$CH_2OR^4$ groups such as those arising from the reaction of an alkyl or aryl glycidyl ether with the proviso that at least one $R^2$ is not hydrogen or methyl;

each $R^3$ is independently —H, unsubstituted or substituted aryl or alkyl hydrocarbon chains of 1-25 carbons which may be saturated or unsaturated or an ester group —C(=O)$R^5$;

$R^4$ is a branched or linear aryl or alkyl moiety of 1-22 carbons which can be substituted or unsubstituted;

$R^5$ is unsubstituted or substituted aryl or alkyl hydrocarbon chain of 1-25 carbons which may be saturated or unsaturated;

n is an integer of 3-300;

m is an integer of 2-300; and o is an integer of 2-12; and an aqueous phase encapsulated inside a continuous hydrocarbon phase.

DESCRIPTION

The present invention is directed to an improved invert emulsifier comprising a core and pendant groups wherein one of the core or pendant group is hydrophobic and the other is hydrophilic functioning as a shell. More specifically, the present invention is specific to an invert emulsifier comprising substituted ethylene oxide groups wherein the substitutions define the hydrophilicity of portions of the molecule.

Specifically, we provide herein emulsifiers comprising ether linkages which withstand chemical assault under conditions in which ester and amide bonds are cleaved or degraded. These emulsifiers are particularly suitable for use in harsh or demanding environments, such as under strongly acidic conditions at elevated temperatures such as those found in subterranean wells or within the machinery of industrial processes where high temperatures may be encountered. The surfactants described herein also benefit from additional favorable characteristics, such as ease and affordability of synthesis, an anticipated low toxicity, and a low pour point allowing room temperature processing.

The polymeric invert emulsifier of the present invention can be considered to have a core and pendant groups, as a shell, with the core and the terminal ends of the pendant groups having very different properties with regards to hydrophobicity or hydrophilicity. A particularly preferred polymeric invert emulsifier can be defined by Formula 1:

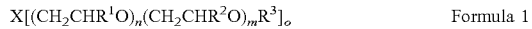
$$X[(CH_2CHR^1O)_n(CH_2CHR^2O)_mR^3]_o \quad \text{Formula 1}$$

wherein the fraction $X[(CH_2CHR^1O)_n]$ is referred to as the core which is preferably hydrophilic and the fraction $(CH_2CHR^2O)_mR^3$ is referred to as the pendant groups which are preferably hydrophobic.

In Formula 1;

X is a linking group preferably derived from a polyol or polyamine wherein at least two alcohol or amine hydrogens are replaced with —$(CH_2CHR^1O)_n(CH_2CHR^2O)_mR^3$;

each $R^1$ is independently —H or —$CH_3$, preferably H;

each $R^2$ is independently —H, branched or linear aryl or alkyl moieties of 1-22 carbons which can be unsubstituted or substituted, and may also be —$CH_2OR^4$ groups such as those arising from the reaction of an alkyl or aryl glycidyl ether with the proviso that at least one $R^2$ is not hydrogen or methyl;

each $R^3$ is independently —H, unsubstituted or substituted aryl or alkyl hydrocarbon chain of 1-25 carbons which may be saturated or unsaturated, with H or hydrocarbon chains of 1-3 carbons being preferred, or an ester group —$C(=O)R^5$;

$R^4$ is a branched or linear aryl or alkyl moiety of 1-22 carbons which can be substituted or unsubstituted;

$R^5$ is unsubstituted or substituted aryl or alkyl hydrocarbon chain of 1-25 carbons which may be saturated or unsaturated;

n is an integer of 3-300;

m is an integer of 2-300 and preferably 3-300; and o is an integer of 2-12.

The linking group, designated X in Formula 1, is selected from polyols and polyamines comprising at least two reactive alcohol or amine hydrogens. The linking group may comprise a linear or branched, optionally substituted, alkyl of 3-100 carbons. In one embodiment, all of the labile alcohol or amine hydrogens are derivatized to form a pendant group attached thereto, however in other embodiments alcohols and/or amines remain to increase the hydrophilicity of the core. Particularly preferred linking groups are selected from the group consisting of ethylene glycol, ethylene diamine, ethylene triamine, glycerin, trimethylol propane, pentaerythritol, sorbitol, sorbitan, diglycerol, triglycerol, higher polyglycerols, and polysaccharides or other polyols such as polyvinyl alcohol with a molecular weight of up to 400 Da.

The polymeric invert emulsifier has a preferred molecular weight of at least 1,000 to 20,000 Da and more preferably 3,500-20,000 Da. The core has a preferred molecular weight of at least 500 Da.

The polymeric invert emulsifiers are generally liquid formulations, and can be used to form emulsions at room temperature without the use of solvents or additional additives. These surfactants can be used to form invert emulsions with unexpectedly high levels of water or aqueous phase and are suitable for use with up to or above 95 wt % aqueous phase if necessary. They are therefore suitable as a polymeric invert emulsifiers offering a wide range of uses across many applications.

The polymeric invert emulsifiers are suitable for use in highly acidic environments, alkaline environments, or otherwise corrosive aqueous fluids. Applications would include the preparation of hydrochloric acid emulsified into hydrocarbons such as diesel for acidizing applications in oil recovery.

The polymeric invert emulsifiers of the present invention have a low viscosity and are easily pourable at common ambient temperatures, thereby allowing for use at low temperatures. Emulsification at temperatures as low as 5° C. can be easily achieved.

The polymeric invert emulsifiers of the present invention have unique solubilization/compatibilization effects for synthetic and natural organic base fluids containing a wide-variety of additives that include, but not limited to: surfactants, lubricity additives, wetting agents, thickeners, and anticorrosive additives.

These polymeric invert emulsifiers are also particularly suitable for use in agricultural applications to formulate emulsifiers and dispersants for use with herbicides, fungicides, insecticides, etc.

They may be further blended with other emulsifiers and cosurfactants thereby allowing for modification of the hydrophilic/lipophilic balance (HLB) and/or overall performance of the emulsifier package. Preferred cosurfactants include, but are not limited to, alcohol alkoxylates and their sulfates or phosphate esters. Particularly preferred alkoxylated phosphate esters include oleyl alcohol reacted with three to seven moles of ethylene oxide and phosphated. Other suitable alcohols include, but are not limited to, C6-C24 linear and branched alcohols, such a lauryl alcohol, stearyl alcohol, tridecyl alcohol, and mixtures thereof. The phosphating reaction may be carried out using suitable phosphating agents known in the art, such a phosphorous pentoxide or polyphosphoric acid. In some cases, propoxylation of these cosurfactants and coemulsifiers by use of propylene oxide may also be desirable, especially for manipulating the surfactant's HLB or pour point.

These polymeric invert emulsifiers are capable of producing inverse emulsions when incorporated at low levels. The amount of polymeric invert emulsifier suitable to function adequately can be as low as 0.1 wt % up about 5 wt % based on the total weight of the total emulsion. Below about 0.1 wt % there is insufficient emulsifying and above about 5 wt % any additional polymeric invert emulsifier provides diminishing returns. It is particularly preferred to use about 0.5 wt % to about 1.5 wt % polymeric invert emulsifier. About 1 wt % polymeric invert emulsifier of the present invention is suitable to maintain oil as the external phase in a mixture of 30% oil and 60% aqueous phase although the aqueous phase may comprise up to 95% of the total emulsion. The inventive polymeric invert emulsifiers have been demonstrated to provide stable emulsions when used to emulsify 70%-80% of aqueous HCl (28% HCl) into 20-30% of diesel fuel as the hydrocarbon at temperatures of up to 100° C. or more.

EXAMPLES

Example 1

In a 150 mL flask were combined 30 g of glycerin alkoxylated with 26 ethylene oxide groups with 840 Da referred to herein as POE(26) glycerin, available from Ethox Chemicals, LLC as Ethox 2988, and 1 g of solid KOH. This mixture was warmed and stirred until the KOH dissolved. To the mixture 190 g of epoxydodecane was added portion wise. The reaction was stirred under nitrogen atmosphere at 130° C. for 4 hours to provide a polymeric invert emulsifier.

The polymeric invert emulsifier was found to make a highly stable HCl emulsion in diesel fuel. For this emulsion, 2 g of the surfactant were dissolved in 28 g of diesel fuel. With agitation, 70 g of 28% HCl were added slowly. This formed an emulsion that was stable overnight at 75° C. and for several hours at 90° C. In contrast, an emulsion made from a similar surfactant incorporating ester bonds was stable for less than two hours under the same conditions.

Example 2

A polymeric invert emulsifier was prepared using alkyl glycidyl ethers. In this reaction, 75 g of POE(26) glycerin and 370 g of C1214 alkyl glycidyl ether (Modifier 8 available from Hexion, CAS 68609-97-2) were reacted at 140° C. using 1.29 g of an alkoxylation catalyst for 16 hours. This emulsifier thus prepared also produced highly stable invert emulsions where hydrochloric acid constituted the internal phase.

Example 3

A polymeric invert emulsifier was prepared using alkyl glycidyl ethers with a base catalyst. In this reaction, 75 g of POE(26)glycerin and 370 g of C1214 alkyl glycidyl ether (Modifier 8 available from Hexion, CAS 68609-97-2) were reacted at 120° C. for 48 hours using 2.5 g of concentrated potassium hydroxide solution. This emulsifier thus prepared also produced highly stable invert emulsions where hydrochloric acid constituted the internal phase.

Example 8

In a 1 L flask, 75 g of POE(17) glycerin was heated to 80° C. with 0.6 g of solid KOH under a nitrogen blanket. 75 g of epoxydodecane was then added, resulting in a temperature rise to 160° C. After cooling to 100° C., an additional 150 g of epoxydodecane was added. After stirring at 100° C. overnight, the reaction was cooled, and a viscous oil resulted.

2 g of the viscous oil was mixed with 98 g of diesel oil, the solution was found to form a stable acid-in-oil emulsion with 25% HCl in water. These emulsions were stable for several days to weeks at temperatures up to 100° C., and consisted of 70-90% HCl solution.

Example 9

150 g of POE(17) glycerin was reacted with 525 g C1214 glycidyl ether, obtained from Dow as DER 721 or Polypox R24, in the presence of a alkoxylation catalyst at 175° C. for 16 hours. Upon cooling, a hazy viscous liquid formed. When 2 g of the formed polymeric invert emulsifier was mixed with 98 g of diesel oil, the solution was found to form stable acid-in-oil emulsions with 25% HCl in water. These emulsions were stable for several days to weeks at temperatures up to 100° C., and consisted of 70-90% HCl solution.

The invention has been described with particular reference to preferred embodiments without limit thereto. One of skill in the art would realize additional embodiments and improvements which are not specifically enumerated but which are within the scope of the invention as specifically set forth in the claims appended hereto.

The invention claimed is:

1. A polymeric invert emulsifier defined by Formula 1:

$$X[(CH_2CHR^1O)_n(CH_2CHR^2O)_mR^3]_o \qquad \text{Formula 1}$$

wherein X comprises at least one unreacted hydroxyl or amine;

each $R^1$ is independently —H or —$CH_3$;

each $R^2$ is independently —H, unsubstituted or substituted branched aryl moiety of 1-22 carbons; or unsubstituted or substituted linear aryl moiety of 1-22 carbons; or unsubstituted or substituted branched alkyl moiety of 1-22 carbons; or unsubstituted or substituted linear alkyl moiety of 1-22 carbons; or —$CH_2OR^4$ with the proviso that at least one $R^2$ is not hydrogen or methyl;

each $R^3$ is independently —H, unsubstituted or substituted saturated or unsaturated aryl hydrocarbon of 1-25 carbons; or unsubstituted or substituted saturated or unsaturated alkyl hydrocarbon of 1-25 carbons; or an ester group —C(=O)$R^5$;

$R^4$ is a substituted or unsubstituted branched aryl moiety of 1-22 carbons; or a substituted or unsubstituted linear aryl moiety of 1-22 carbons; or a substituted or unsubstituted branched alkyl moiety of 1-22 carbons; or a substituted or unsubstituted linear alkyl moiety of 1-22 carbons;

$R^5$ is a substituted or unsubstituted saturated or unsaturated aryl moiety of 1-25 carbons; or a substituted or unsubstituted saturated alkyl moiety of 1-25;

n is an integer of 3-300;

m is an integer of 2-300; and o is an integer of 2-12.

2. The polymeric invert emulsifier of claim 1 wherein said X comprises a linear or branched alkyl of 3-100 carbons.

3. The polymeric invert emulsifier of claim 1 wherein at least one $R^1$ is —H.

4. The polymeric invert emulsifier of claim 3 wherein each $R^1$ is —H.

5. The polymeric invert emulsifier of claim 1 wherein m is an integer of 3-300.

6. The polymeric invert emulsifier of claim 1 wherein $R^3$ is independently —H or a hydrocarbon chain of 1-3 carbons.

7. The polymeric invert emulsifier of claim 1 having a molecular weight of 1,000-20,000 Da.

8. The polymeric invert emulsifier of claim 1 comprising at least one unreacted hydroxyl.

9. The polymeric invert emulsifier of claim 8 comprising at least one unreacted amine.

10. A polymeric invert emulsifier defined by Formula 1:

$$X[(CH_2CHR^1O)_n(CH_2CHR^2O)_mR^3]_o \qquad \text{Formula 1}$$

wherein X is a linking group derived from an organic compound containing at least two hydroxyl or amine groups capable of reacting with ethylene oxide;

each $R^1$ is independently —H or —$CH_3$;

each $R^2$ is independently —H, unsubstituted or substituted branched aryl moiety of 1-22 carbons; or unsubstituted or substituted linear aryl moiety of 1-22 carbons; or unsubstituted or substituted branched alkyl moiety of 1-22 carbons; or unsubstituted or substituted linear alkyl moiety of 1-22 carbons; or —$CH_2OR^4$ with the proviso that at least one $R^2$ is not hydrogen or methyl;

each $R^3$ is independently —H, unsubstituted or substituted saturated or unsaturated aryl hydrocarbon of 1-25 carbons; or unsubstituted or substituted saturated or unsaturated alkyl hydrocarbon of 1-25 carbons; or an ester group —C(=O)$R^5$;

$R^4$ is a substituted or unsubstituted branched aryl moiety of 1-22 carbons; or a substituted or unsubstituted linear aryl moiety of 1-22 carbons; or a substituted or unsubstituted branched alkyl moiety of 1-22 carbons; or a substituted or unsubstituted linear alkyl moiety of 1-22 carbons;

$R^5$ is a substituted or unsubstituted saturated or unsaturated aryl moiety of 1-25 carbons; or a substituted or unsubstituted saturated alkyl moiety of 1-25;

n is an integer of 3-300;

m is an integer of 2-300; and o is an integer of 2-12; and further comprising a second emulsifier.

11. The polymeric invert emulsifier of claim 10 wherein X is a derived from a polyol or polyamine wherein at least two hydroxyl or amine hydrogens are replaced with —$(CH_2CHR^1O)_n(CH_2CHR^2O)_mR^3$.

12. The polymeric invert emulsifier of claim 11 wherein X is a derived from a polyol or polyamine wherein at least three hydroxyl or amine hydrogens are replaced with —$(CH_2CHR^1O)_n(CH_2CHR^2O)_mR^3$.

13. The polymeric invert emulsifier of claim 10 wherein all of the labile hydroxyl or amine hydrogens of said X are replaced with $(CH_2CHR^1O)_n(CH_2CHR^2O)_mR^3$.

14. The polymeric invert emulsifier of claim 10 wherein said X is a derivative of a material selected from the group consisting of ethylene glycol, ethylene diamine, glycerin, trimethylol propane, pentaerythritol, sorbitol, and polyvinyl alcohol.

15. The polymeric invert emulsifier of claim 10 wherein said second emulsifier is a phosphate ester, sulfate, alcohol alkoxylates, alcohol alkoxylate sulfate or alcohol alkoxylate phosphate ester.

16. The polymeric invert emulsifier of claim 15 wherein said second emulsifier is selected from an oleyl alcohol wherein said oleyl alcohol is reacted with three to seven moles of ethylene oxide and phosphate or C6-C24 linear and branched alcohols.

17. The polymeric invert emulsifier of claim 10 wherein said second emulsifier is selected from ethoxylates of lauryl alcohol, ethoxylates of stearyl alcohol, ethoxylates of tridecyl alcohol, ethoxylates of oleyl alcohol, and mixtures thereof.

18. The polymeric invert emulsifier of claim 10 wherein at least one $R^1$ is —H.

19. The polymeric invert emulsifier of claim 18 wherein each $R^1$ is —H.

20. The polymeric invert emulsifier of claim 10 wherein m is an integer of 3-300.

21. The polymeric invert emulsifier of claim 10 wherein $R^3$ is independently —H or a hydrocarbon chain of 1-3 carbons.

22. The polymeric invert emulsifier of claim 10 having a molecular weight of 1,000-20,000 Da.

23. An emulsion comprising the polymeric invert emulsifier of claim 1.

24. The emulsion of claim 23 comprising an aqueous phase encapsulated in a continuous hydrocarbon phase.

25. The emulsion of claim 24 wherein said aqueous phase is an acidic solution.

26. The emulsion of claim 25 wherein said aqueous phase is a caustic or alkaline solution.

27. An emulsion comprising the polymeric invert emulsifier of claim 10.

28. The emulsion of claim 27 wherein comprising an aqueous phase encapsulated in a continuous hydrocarbon phase.

29. The emulsion of claim 28 wherein said aqueous phase is an acidic solution.

30. The emulsion of claim 28 wherein said aqueous phase is a caustic or alkaline solution.

* * * * *